(12) United States Patent
Shoeb et al.

(10) Patent No.: US 10,159,428 B1
(45) Date of Patent: Dec. 25, 2018

(54) INSTRUMENTED HANDHELD TOOL FOR MEASURING UPPER EXTREMITY FREEZING

(71) Applicant: Verily Life Sciences LLC, Mountain View, CA (US)

(72) Inventors: Ali Shoeb, Mill Valley, CA (US); Anupam J. Pathak, Mountain View, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 376 days.

(21) Appl. No.: 15/013,626

(22) Filed: Feb. 2, 2016

(51) Int. Cl.
*A61B 5/00* (2006.01)
*A61B 5/11* (2006.01)

(52) U.S. Cl.
CPC .......... *A61B 5/1101* (2013.01); *A61B 5/7275* (2013.01); *A61B 5/7282* (2013.01)

(58) Field of Classification Search
CPC .............. A61B 5/11; A61B 5/1101; A61B 5/1123–5/26; A61B 5/7275; A61B 5/7282
See application file for complete search history.

(56) References Cited

U.S. PATENT DOCUMENTS

| | | | |
|---|---|---|---|
| 5,573,011 A | 11/1996 | Felsing | |
| 5,772,611 A * | 6/1998 | Hocherman | A61B 5/1101 600/595 |
| 8,702,629 B2 | 4/2014 | Giuffrida et al. | |
| 8,981,765 B2 * | 3/2015 | Sano | A61B 5/1125 324/207.11 |
| 9,615,776 B2 * | 4/2017 | Smith | G06K 9/00536 |
| 2014/0303508 A1 | 10/2014 | Plotnik-Peleg et al. | |

FOREIGN PATENT DOCUMENTS

| | | |
|---|---|---|
| EP | 19998849 | 12/2014 |
| WO | 2013022890 | 2/2013 |

* cited by examiner

*Primary Examiner* — Max Hindenburg
(74) *Attorney, Agent, or Firm* — Christensen O'Connor Johnson Kindness PLLLC (57) ABSTRACT

An apparatus, system and process for measuring, tracking, and analyzing unintentional muscle movements associated with upper body freezing of a user while using a handheld tool are described. The method may include receiving signals from a motion sensor of a handheld tool, the signals indicating motions of the handheld tool when used by a user during an activity. The method may also include analyzing the motions of the handheld tool. The method may also include detecting motions of the handheld tool having one or more predetermined characteristics. Furthermore, the method can include determining that the user experienced an upper extremity freezing while using the handheld tool during the activity based on the detected one or more predetermined characteristics.

24 Claims, 5 Drawing Sheets

INSTRUMENTED HANDHELD TOOL FOR MEASURING UPPER EXTREMITY FREEZING

TECHNICAL FIELD

This disclosure relates generally to unintentional muscle movements, and in particular but not exclusively, relates to the measurement and tracking of upper extremity freezing.

BACKGROUND INFORMATION

Movement disorders are often caused by chronic neurodegenerative diseases such as Parkinson's Disease ("PD") and Essential Tremor ("ET"). Both of these conditions are currently incurable and cause unintentional muscle movements or human tremors—uncontrollable rhythmic oscillatory movements of the human body. In many cases human tremors can be severe enough to cause a significant degradation in quality of life, interfering with daily activities/tasks such as eating, drinking, or writing.

Patients with movement disorders are typically diagnosed in a clinic using scales such as the Fahn-Tolosa-Marin Tremor Rating Scale for ET or the Unified Parkinson Disease (UPDRS) rating scale for PD. Both of these scales require a trained neurologist to complete and often rely on subjective assessments that occur over a brief period of time in the practitioner's office. Symptom severity at home is typically evaluated from the patient's self-reporting, which is also highly subjective and prone to error.

A particular incapacitating problem associated with chronic neurodegenerative diseases involves freezing, in the upper and/or lower extremities of a patient. Lower extremity freezing and other gait disorders can result in falls and injuries, while upper extremity freezing can hamper day to day activities such as eating and brushing teeth. Thus, upper and/or lower extremity freezing can severely impact quality of life. Furthermore, if a neurologist is attempting to treat a patient for one or more of these conditions, it is often difficult to assess the severity, length, and frequency of freezing events, and whether treatments are helping with such freezing events. Some devices have been used to track lower extremity freezing, but require bulky and obtrusive sensors that a user must wear to track gait. This creates significant challenges when diagnosing, developing and evaluating long-term treatments or interventions for these diseases.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Embodiments of an apparatus, system and process for measuring, tracking, and analyzing unintentional muscle movements associated with upper body freezing of a user while using a handheld tool to perform an ordinary activity are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1A:
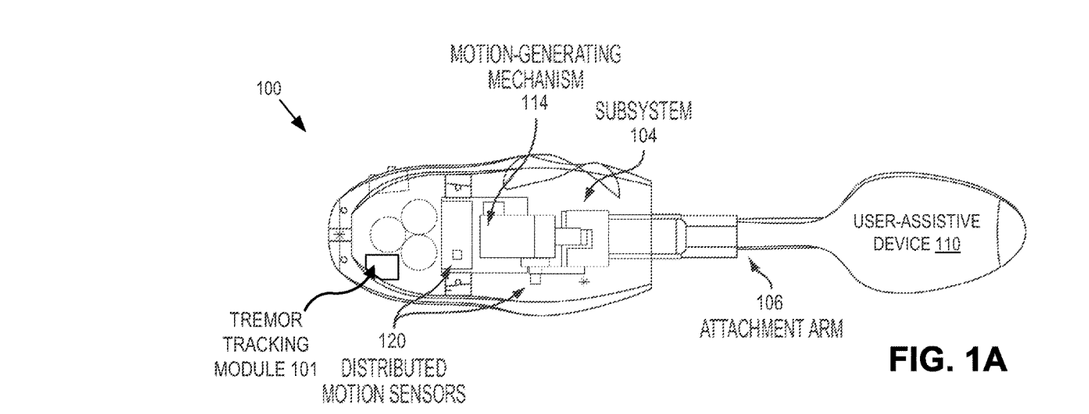
FIG. 1A is a cross-sectional illustration of a handheld tool that measures and tracks unintentional muscle movements, in accordance with an embodiment of the disclosure.
Figure 1B:
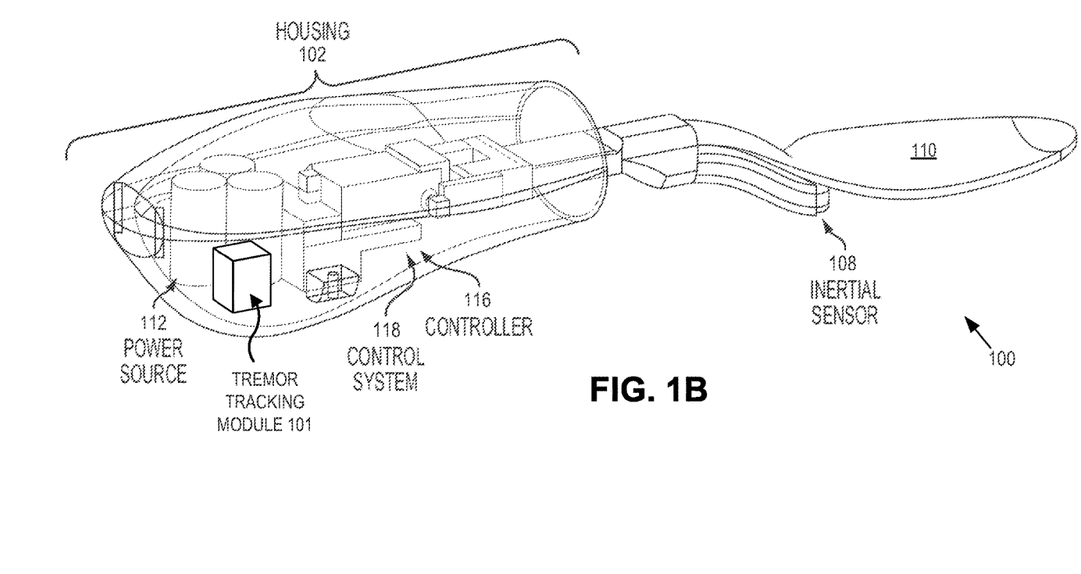
FIG. 1B is a perspective view illustration of the handheld tool that measures and tracks unintentional muscle movements, in accordance with an embodiment of the disclosure.

FIGS. 1A and 1B illustrate a handheld tool 100 that measures and tracks unintentional muscle movements, in accordance with an embodiment of the disclosure. FIG. 1A is a cross-sectional illustration of handheld tool 100 while FIG. 1B is a perspective view illustration of the same. Handheld tool 100 is also capable of detecting and compensating for unintentional muscle movement (tremors); however, it should be appreciated that various embodiments need not include the mechanisms and associated sensors for tremor compensation to implement the measurement, tracking, and/or diagnosing of upper and/or lower extremity freezing, even though both features are incorporated into the illustrated embodiment of handheld tool 100. Accordingly, the illustrated embodiment of handheld tool 100 includes a subsystem for measuring and tracking unintentional user movements (e.g., a tremor tracking module) and a subsystem for detecting and compensating for those same unintentional user movements. These subsystems may have distinct components, or share some components such as power systems, memory, a controller, and may even share one or more sensors. In some embodiments, one or more components of the subsystem for detecting and compensating for unintentional movements may be omitted.

Handheld tool 100 includes a housing 102, which functions as a handle for holding handheld tool 100. Handheld tool 100 also includes an attachment arm 106 coupled to the housing 102. Attachment arm 106 is configured to accept a user-assistive device 110 (e.g., a spoon in the illustrated embodiment) to its end distal from housing 102. Handheld tool 100 further includes a tremor tracking module ("TTM")

101 for measuring and tracking unintentional user movements, such as tremors, freezing events, etc. One or more components of TTM 101 are rigidly attached to housing 102 to measure and track unintentional movements of the handle that the user holds. FIGS. 1A and 1B illustrate TTM 101 as a single block within housing 102; however, in other embodiments, TTM 101 includes several functional items that may assume a variety of different form factors and may further be spread throughout housing 102. Furthermore, TTM 101 may include, or be coupled with, additional elements (not shown) such as user interfaces with the TTM 101 to annotate or signal certain motion events, such as freezing events. In embodiments, the user interfaces could include one or more of buttons, a capacitive touch panel, or other interfaces for initiating and generating annotations as discussed herein.

The illustrated embodiment of handheld tool 100 further includes a subsystem 104 for detecting and compensating for unintentional user movements, such as tremors, of user-assistive device 110. In the illustrated embodiment, subsystem 104 includes at least one inertial sensor 108 placed along attachment arm 106 to measure absolute movement of attachment arm 106 and user-assistive device 110. Subsystem 104 further includes a portable power source 112, a motion-generating mechanism 114, a controller 116, a control system 118, and at least one distributed motion sensor 120 for measuring relative motion of attachment arm 106 relative to housing 102. As mentioned above, TTM 101 may share one or more of the components of subsystem 104 (e.g., power source 112, controller 116, etc.). In other embodiments, one or more of the components of subsystem 104 for compensating tremor motions may also be omitted (e.g., inertial sensor 108, motion-generating mechanism 114, etc.) while still implementing the user motion measurement and tracking functionality disclosed herein.

In one embodiment, attachment arm 106 is integrated with a specific type of user-assistive device 110 (spoon illustrated). In other embodiments, attachment arm 106 can receive a variety of different user-assistive devices 110 in a variety of ways including but not limited to a friction, snap, or other form of locking mechanism. Portable power source 112 may utilize a variety of options including but not limited to a rechargeable battery, a solar panel, etc.

The at least one inertial sensor 108 and the at least one distributed motion sensor 120 detect unintentional muscle movements and measure signals related to these unintentional muscle movements that are created when a user adversely affects motion of user-assistive device 110. These sensors also detect the motion of the stabilized output relative to the housing 102. Control system 118 sends voltage commands in response to the signals to the motion-generating mechanism 114 through the controller 116 to cancel the user's tremors or unintentional muscle movements. This cancellation maintains and stabilizes a position of the user-assistive device 110, keeping it centered relative to the housing 102.

One of ordinary skill in the art readily recognizes that a system and method in accordance with the present disclosure may utilize various implementations of controller 116, at least one inertial sensor 108, at least one distributed motion sensor 120, and control system 118 and that would be within the spirit and scope of the present disclosure. In one embodiment, controller 116 comprises an electrical system capable of producing an electrical response from sensor inputs such as a programmable microcontroller a field-programmable gate array (FPGA), an application specific integrated circuit ("ASIC"), or otherwise. In one embodiment, controller 116 comprises an 8-bit ATMEGA8A programmable microcontroller manufactured by Atmel due to its overall low-cost, low-power consumption and ability to be utilized in high-volume applications.

In one embodiment, the at least one inertial sensor 108 is a sensor including but not limited to an accelerometer, gyroscope, or combination of the two. In one embodiment, the at least one distributed motion sensor 120 is a contactless position sensor including but not limited to a hall-effect magnetic sensor. In one embodiment, the control system 118 is a closed-loop control system.

The closed-loop control system senses motion and acceleration at various points along handheld tool 100 and feeds detailed information into a control algorithm that moves motion-generating mechanism 114 appropriately to cancel the net effect of a user's unintentional muscle movements and thus stabilize the position of user-assistive device 110.

One of ordinary skill in the art will readily recognize that an apparatus, a system, or method as described herein may be utilized for a variety of applications. For example, various different user-assistive devices 110 may include a manufacturing tool, a surgical tool, a kitchen utensil (e.g., fork, knife, spoon), a sporting tool, a yard tool, a grooming tool (e.g., comb, nail clippers, tweezers, make-up applicator, etc.), or a dental hygiene tool (e.g., toothbrush, flossing tool, etc.). Thus, handheld tool 100 may be useful in not only improving the quality of life for the multitudes of individuals suffering from neurological motion disorders, but also in assisting in a variety of applications where physiological tremor is an issue including but not limited to manufacturing, surgical and public safety applications.

In one embodiment, handheld tool 100 stabilizes user-assistive device 110 about a neutral position (for example, θ=0 may be selected or otherwise) using the at least one inertial sensor 108. To achieve this, the position of user-assistive device 110 is sensed along with the angle θ. For this position sensing, the at least one inertial sensor 108 is placed along the attachment arm 106 and is used to measure the absolute motion of the user-assistive device 110 while providing low noise and sufficient sensitivity for the application. The direct sensor placement of the at least one inertial sensor 108 along attachment arm 106 gives a unique advantage to handheld tool 100 as it is extremely robust and does not rely on inverse kinematics/dynamics which may change depending on usage. Thus, as aforementioned, a variety of objects can be used to implement user-assistive device 110 without the need to pre-determine and pre-program the length and weight of user-assistive device 110 into the controller 116.

In the illustrated embodiment, the at least one distributed motion sensor 120 is located within the housing 102 which is located at the base of the handheld tool 100. The at least one distributed motion sensor 120 measures the relative motion of attachment arm 106 relative to the housing 102, wherein user-assistive device 110 is kept at a center position relative to housing 102. In one embodiment, the at least one distributed motion sensor 120 is at least one contactless hall-effect position sensor that provides angular feedback for control system 118 and relies on a changing magnetic field that is dependent on the actuation angle.

The changing magnetic field is detected by a strategically placed integrated circuit (IC) located within the at least one distributed motion sensor 120, whose analog output is read by controller 116, providing a completely non-contact angular detection that is capable of withstanding a large number of cycles. The at least one distributed motion sensor 120, with its contactless sensing methods, provides improved reliability over conventional direct-contact sensing methods such as potentiometers that wear over time.

In one embodiment, handheld tool 100 uses a combination of coreless micro-motors and miniature gear-reduction systems coupled to the coreless micro-motors using a coupling mechanism to implement motion-generating mechanism 114. Significant force of up to 10 newtons (N) can also be produced with these coreless micro-motors at the required tremor frequency of 0-5 hertz (Hz) through the use of a low-cost miniature gear-reduction system, with a total weight of only 6.5 grams (g). Furthermore, the power drawn from this technology is low, estimated at 0.5 watts (W).

Figure 2:
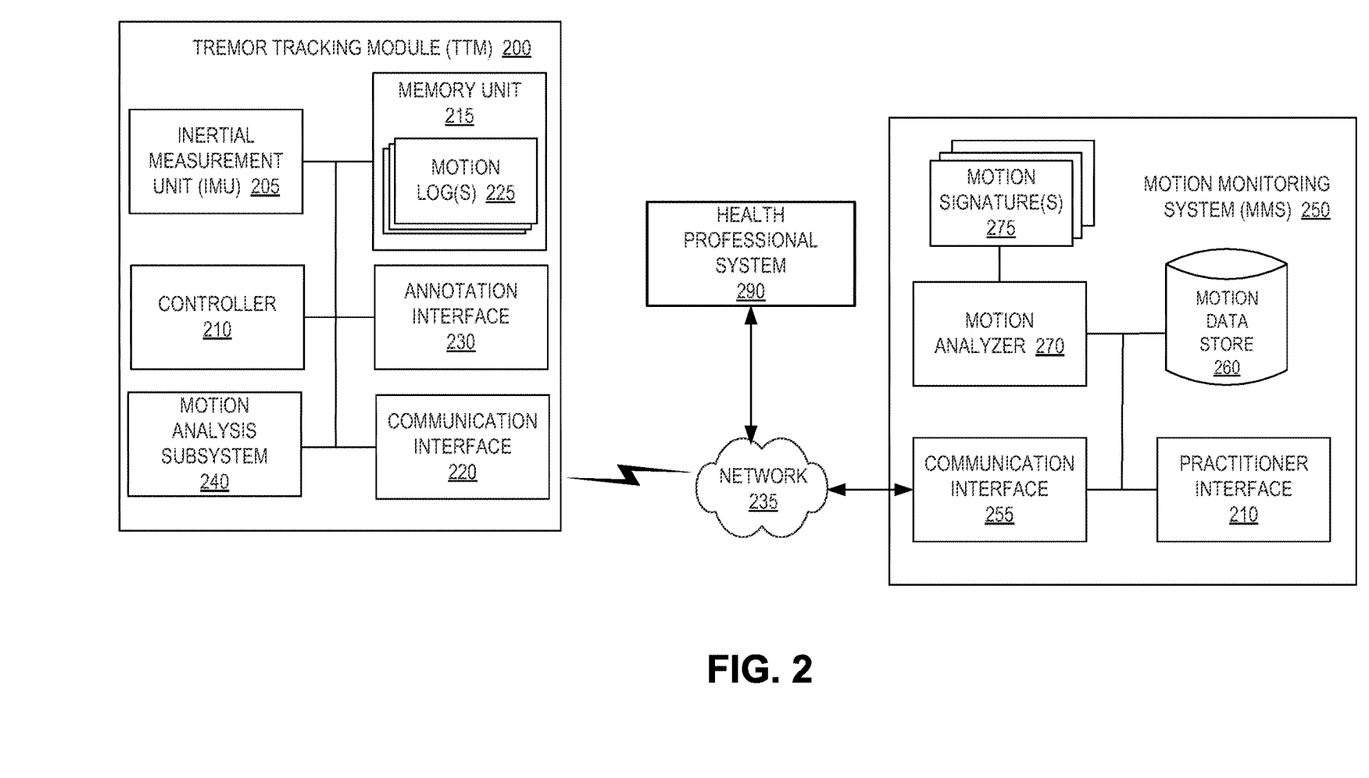
FIG. 2 is a functional block diagram illustrating a tremor tracking module and a motion monitoring system, in accordance with an embodiment of the disclosure.

FIG. 2 is a functional block diagram illustrating a TTM 200 and a motion monitoring system (MMS) 250, in accordance with an embodiment of the disclosure. TTM 200 is one possible implementation of TTM 101 illustrated in FIGS. 1A and 1B. The illustrated embodiment of TTM 200 includes an inertial measurement unit ("IMU") 205, a controller 210, a memory unit 215, a communication interface 220, and an annotation interface 220. The illustrated embodiment of the MMS 250 includes a communication interface 255, a motion analyzer 270, motion data store 260, practitioner interface 280, and one or more motion signatures 275.

IMU 205 is disposed in rigid contact with housing 102 to directly measure the tremor motions, as well as other motions, of the handle and by extension the tremor motions of the user's hand. TTM 200 facilitates the detection and measurement certain motion events, such as upper extremity freezing, while a user is performing an everyday task, such as eating or grooming (e.g., applying makeup). This is an important distinction over conventional in-clinic evaluations that simply measure the tremor of a hand that a patient is attempting to hold steady. Measurement and tracking of user motions while the patient is performing an everyday task measures the condition under real-world scenarios that are most adversely impacted by human tremors, freezing, etc. Accordingly, TTM 200 can be embedded within everyday items or tools that are used routinely by patients to accurately measure and track their condition, such as the handheld tool illustrated above in FIG. 1, as well as other devices such as fitness trackers, smart watches, pedometers, etc. This can lead to improved evaluations.

Not only can handheld tool 100 measure and track user motions during a routine task, but it can conveniently do so over a period of time to obtain a more reliable dataset for statistical analysis. Furthermore, handheld tool 100 can be used at home where the user is more relaxed and under less stress than a formal evaluation in a practitioner's office. Data collection within the home environment along with larger datasets than can be obtained in-clinic, can provide more reliable data for evaluation of a patient's symptoms. Improved evaluation and diagnosis of the patient's various motion events, such as frequency, duration, and magnitude of upper extremity freezing, facilitate improved treatments and interventions of the various diseases and the conditions that cause human tremors.

IMU 205 may be implemented using variety of devices that measure motions of the handle of handheld tool 100. For example, IMU 205 may include one or more accelerometers that measure linear accelerations. In one embodiment, IMU 205 includes accelerometers capable of measuring translational accelerations of the handle in three orthogonal dimensions (e.g., x, y, and z dimensions). In one embodiment, IMU 205 includes a gyroscope to measure rotational motions (e.g., angular velocity about an axis) of the handle of handheld tool 100. In various embodiments, the gyroscope may be capable of measuring the rotational motions about one, two, or three orthogonal rotational axes. In one embodiment, IMU 205 includes a magnetometer to measure motions of the handle relative to a magnetic field (e.g., Earth's magnetic field or other externally applied magnetic field). In various embodiments, IMU 205 may include various combinations of some or all of the above listed motion measuring devices, as well as other sensors (e.g., pressure sensors, temperature sensors, moisture sensors, etc.), for capturing different characteristics of user motions. Furthermore, these sensors may be disposed together on a common substrate that is rigidly attached to housing 102, or disposed throughout housing 102.

Controller 210 is communicatively coupled to IMU 205 and memory unit 215 to read motion data output from IMU 205 and store the motion data into memory unit 215. The motion data is collected over a period of time and may be organized into one or more motion log(s) 225. For example, the motion data may be collected while the user performs an individual task, over the course of a day, a week, or other period of time. In one embodiment, motion log(s) 225 may contain enough information about the user's motions (linear accelerations, rotational velocities, durations of these accelerations/velocities, orientation relative to a magnetic field, etc.), based upon the motion data output from IMU 205, to recreate those motions using motion log(s) 225. In one embodiment, motion log(s) 225 may also record date/time stamps of when the motion data was collected and even include identifiers indicating the type of user-assistive device 110 that was attached to the handheld 100 when the motion data was collected. The type identifier provides an indication of the activity (e.g., eating with a fork, knife, or spoon, etc.) being performed by the user when the motion data was collected. This activity information and time/date stamps may be useful for the practitioner when evaluating the patient's motion log(s) 225 to determine if the patient's tremors, freezing events, or other unintentional movements, correlate to particular activities or time of day. In yet other embodiments, motion log(s) 225 may also record battery voltage as a function of date/time, which may be used to analyzing system performance and battery usage. Tracking battery voltage is a sort of proxy for the amount of effort exerted by motion-generating mechanism 114 to stabilize user-assistive device 110. As such, tracking battery voltage or battery consumption correlates to the degree of a user's tremors since battery consumption will rise with increased tremors.

In one embodiment, TTM 200 also includes an annotation interface 230. Annotation interface 230 enables a user, or other individual, to annotate one or more user motions. Such an annotation interface 230 can include a user selectable button, switch, knob, etc. Furthermore, annotation interface 220 may monitor IMU 205 in order to detect specific types of motions, such as a "shake shake" command, in which a user purposefully moves a handheld tool in a known way. In one embodiment, the annotation interface 230 enables a user, or other person associated with a user, to mark certain motion events within the motion data stored in motion log(s) 225. For example, in response to a freezing event, such as upper and/or lower extremity freezing, gait problems, balance problems, etc., a user or person near the user can activate the annotation interface 230 to mark the occurrence of the event in the motion log 225. In one embodiment, an annotation stored within the motion log(s) 225, as will be discussed below, can signal that certain user motions are significant and/or associated with specific motion events, such as freezing events.

Controller 210 may be implemented with a programmable microcontroller, an FPGA, an ASIC, or other devices capable of executing logical instructions. The logical instructions themselves may be hardware logic, software logic (e.g., stored within memory unit 215 or elsewhere), or a combination of both. Memory unit 215 may be implemented using volatile or non-volatile memory (e.g., flash memory).

Communication interface 220 is communicatively coupled to output the motion log(s) 225 from memory unit 215 to motion monitoring system 250 via network 235 (e.g., the Internet). In one embodiment, communication interface 220 is a wireless communication interface (e.g., Bluetooth, WiFi, etc.). For example, communication interface 220 may establish a wireless link to a user's cellular phone (not shown) which delivers motion log 225 to server 230 via an installed tremor tracking application. The application may enable the user to control privacy settings, add comments about their usage of handheld tool 100, setup automatic periodic reporting of motion log 225, initiate a one-time reporting of motion log 225, along with other user functions. In yet another embodiment, communication interface 220 may be a wired communication port (e.g., USB port). For example, when the user connects handheld tool 100 to a charging dock to charge power source 112, communication interface 220 may also establish a communication session with motion monitoring system 250 for delivery of motion log(s) 225 thereto.

In one embodiment, motion monitoring system 250 may be executed on a server computer system which includes a processor, memory, networking interface(s), and other components typically associated with server computer systems. In one embodiment, communication interface 225 couples motion monitoring system 250 to network 235 via any of the standard protocols for the exchange of information. Furthermore, communication interface 255 receives the reporting of one or more motion log(s) 225 from TTM 200. The received motion log(s) 225 are stored in motion data store 260 and associated with a user of the TTM 200.

In one embodiment, practitioner interface 280 is an interface that enables a medical practitioner associated with treatment of a user of the TTM 220 to receive reports related to freezing events. Practitioner interface 210 may further receive input from a practitioner authorized by the user of the TTM 220 to input additional information associated with the user into motion data store 260, such as medications, treatments, diagnoses, etc. In one embodiment, enabling a practitioner to input such information into the motion data store 260 of MMS 250 is conditioned on authorization by a user. Furthermore, such information may be maintained in motion data store 260 in an encrypted, or otherwise protected, form. As will be discussed in greater detail below, the results of the motion analyzer 270 can be combined with user-specific information (e.g., medications, ongoing treatments, previous diagnosis, etc.) when generating reports by the practitioner interface 280 to a medical practitioner.

In one embodiment, motion analyzer 270 periodically, or in response to a request received from a medical practitioner via practitioner interface 280, analyzes user motions stored in motion data store 260. In order to detect certain motion events, such as upper extremity freezing, motion analyzer 270 analyzes the motion data to detect motions having certain frequencies, amplitudes, durations, as well as other characteristics. In one embodiment, motion analyzer 270 utilizes one or more motion signatures 275 that describe characteristics and/or patterns of interest with respect to user motions. For example, characteristics associated with upper extremity freezing, and described by one of the motion signature(s) 275 can include small amplitude movements that tend to trigger upper limb freezing, which are preceded by hastened movement with a strong amplitude breakdown. As another example, motion signature(s) 275 can include motion characteristics, such as upper limb freezing having a broadband power spectra, including increased energy in a "freeze band" (e.g., 3-8 Hz). As another example, a motion signature from motion signature(s) 275 may have a first motion type, such as a precursor signal that can indicate the start of a freezing event (e.g., upper and/or lower extremity freezing), followed by a second motion type within a predetermined/threshold amount of time, which can signal the occurrence of an event. However, patterns of movements need not be detected to determining that a freezing event has occurred with respect to a user, as motion events may be detected using one or more of the motion signature(s) 275. When motion analyzer 270 detects movements indicative of upper extremity freezing, motion analyzer can store data indicative of the upper extremity freezing, along with a duration and severity of the upper extremity freezing, in motion data store 260.

In one embodiment, practitioner interface 280 periodically, or in response to a request by an authorized medical practitioner, generates freezing reports and transmits those reports to the medical practitioner at health professional system 290 via network 235. In one embodiment, the reports can collect data over a period of time to generate valuable reports for a medical practitioner with respect to a user's ongoing conditions and/or response to treatment. For example, a report can include reports of freezing events, such as frequency of occurrence of upper extremity freezing events, severity of each event, average severity, duration of freezing events, trends with respect to freezing events (e.g., events increasing or decreasing with respect to one or more of frequency, duration, and severity), as well as other statistics associated with freezing events. Furthermore, when patient-specific information is associated with a user, such as medications, ongoing treatments, previous diagnosis, etc., that patient-specific information can be correlated with the freezing event information in the reporting to indicate, for example, freezing events have decreased following a certain medication schedule, freezing events have increased following a certain treatment, correlations with freezing events and estimated or measured medication in the user's bloodstream, correlations between freezing events and tuning parameters set in a neurostimulator used by the user, etc.

In one embodiment, motion analyzer 270 may further predict lower extremity freezing for a user from the corpus of upper extremity freezing data available in motion data store 260. There is mounting scientific evidence of a link and/or correlation between upper extremity and lower extremity freezing. The link is critical since the measurement and analysis of a user's severity, duration, and frequency of upper extremity freezing events can predict that the user is also likely to exhibit lower extremity freezing, such as "freezing of gait" (FOG) freezing. This prediction is very valuable as lower extremity freezing can be linked to falls and severe, debilitating injuries. Therefore, motion analyzer 270 analyzes the corpus of detected upper extremity freezing events for a user, and based on the duration, frequency, and severity of such events can generate a prediction that the user is likely to also exhibit lower extremity freezing. The prediction, along with the basis of the prediction, confidence of the prediction, and other factors associated with the prediction, can be included by the practitioner interface 280 in a freezing report to health professional system 290.

In one embodiment, motion analyzer 270 may refine one or more of the motion signature(s) 275 for a specific user over a period of time. For example, motion analyzer 270 may associate motion data for different freezing events of a user with a certain motion signature having a precursor signal and an event signal. In one embodiment, motion analyzer 270 can employ machine learning analysis to refine the motion signature's precursor and event signals to better reflect a specific user's motions leading up to the motion event (e.g., a user-specific precursor signal motion signature), during the motion event (e.g., a user-specific event signal motional signature), a period of time between the precursor and event signals (e.g., a user threshold time), etc. This can be further refined with user annotations that confirm when certain events, such as freezing events, occur. In embodiments, refined motion signatures can be stored and associated with specific users so that motion analyzer 270 can analyzing subsequent motion data using user-specific motion signatures.

In one embodiment, TTM 200 may include a motion analysis subsystem 240. The motion analysis subsystem 240 may include a motion analyzer, one or more motion signatures, and a practitioner interface, such as those discussed above with respect to MMS 250. In this embodiment, TTM 200 of a handheld tool (e.g., handheld tool 100) may detect freezing events, predict lower extremity freezing from the frequency, severity, and duration of detected upper extremity freezing events, etc. utilizing the motion analysis subsystem 240. In this embodiment, the motion logs would not be transmitted to a remote server with MMS 250, any only periodic or on-demand practitioner reportings would be transmitted to health professional system 290 from TTM 200.

In yet another embodiment, motion monitoring system 250 may be embodied in a user device (not shown), such as a mobile telephone, tablet computer, or other computing system associated with a user of the TTM 200. In this embodiment, TTM 200 could be periodically communicably coupled with the user device, for example to charge the handheld tool having the TTM 200, to transfer motion logs 225, etc. Furthermore, the user device could include MMS 250 instead of a remote server.

Figure 3:
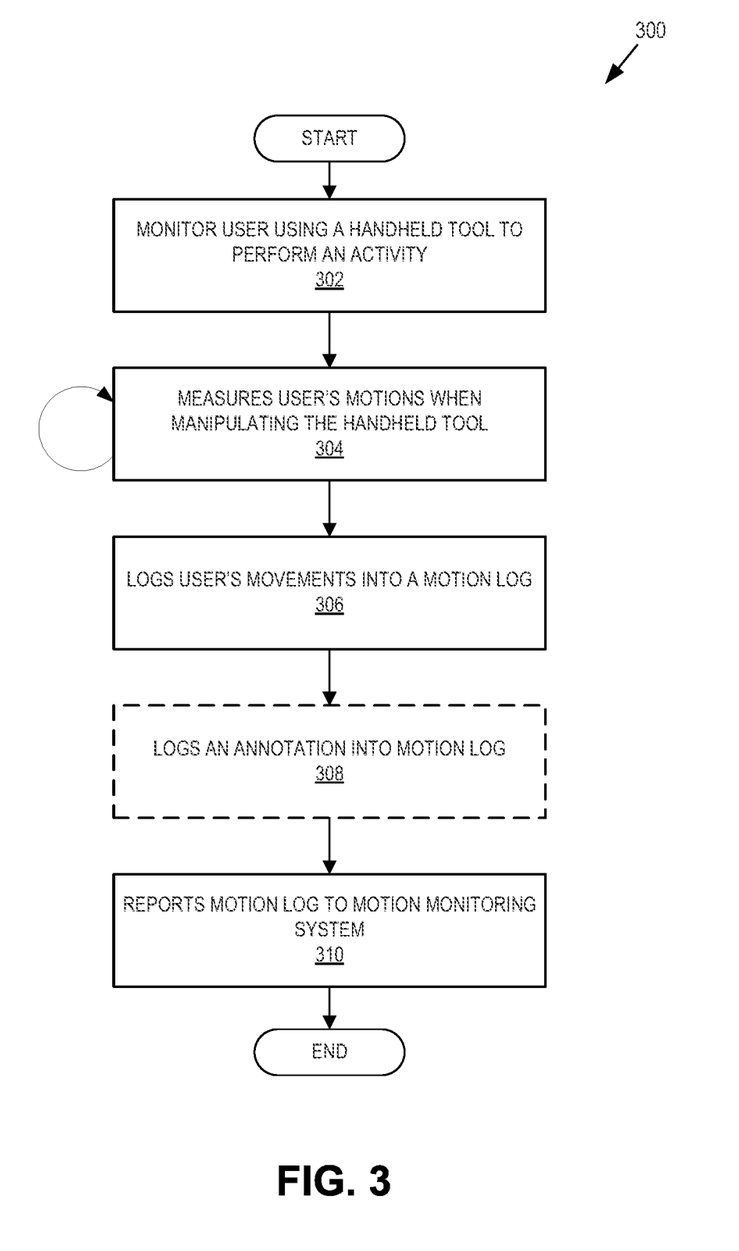
FIG. 3 is a flow chart illustrating a process for measuring and logging unintentional muscle movements using a handheld tool, in accordance with an embodiment of the disclosure.

FIG. 3 is a flow chart illustrating a process for measuring and logging unintentional muscle movements using a handheld tool, in accordance with an embodiment of the disclosure. The process is performed by processing logic that may comprise hardware (circuitry, dedicated logic, etc.), software (such as is run on a general purpose computer system or a dedicated machine), firmware, or a combination. In one embodiment, the process is performed by a tremor tracking module of a handheld tool (e.g., handheld tool 100 of FIG. 1 and TTM 200 of FIG. 2).

Referring to FIG. 3, processing logic begins by monitoring a user using a handheld tool to perform an activity (processing block 302). Processing logic measures patient's motions when manipulating the handheld tool (processing block 304). As discussed above, a handheld tool can include a body and an attachment, where the attachment can be used to perform various data to day tasks (e.g., a spoon attachment used while eating, a toothbrush attachment used while brushing the patient's teeth, etc.). Of course, the handheld tool may used for other non-routine activities, as described above. A tremor tracking module can be included within the handheld tool to directly measure user motions and characteristics of a user with the one or more sensors within the handheld tool, such as accelerometers, gyroscopes, pressure sensors, temperature sensors, etc. Furthermore, in some embodiments, the handheld tool may also perform simultaneous active stabilization to reduce impact of a patient's involuntary movements. In embodiments, processing logic can measure the patient's motions over a period of time at a predetermined sampling rate, such as 25 times per second, 50 times per second, 100 times per second, etc.

Processing logic logs the user's movement into a motion log (processing block 306). For example, the motion data gathered by the one or more sensors may be stored in a memory of the handheld tool, along with timestamps, type of assistance device attached to the handheld tool, etc. indicative of metadata to be associated with specific motion data samples. Processing logic may optionally log an annotation into the motion log (processing block 308). As discussed herein, the annotation is user inputted data, in the form of a motion command or physical user interface selection that indicates certain motion data should be associated with specific tracked user motions. For example, in response to a freezing event, use motion data preceding that event can be explicitly associated with upper extremity freezing by way of a user annotation, such as by associating motions within a threshold time of the annotation, by associating motions having certain predefined characteristics proximate to the annotation, etc.

Processing logic then reports the motion log to a motion monitoring system (processing block 310). In one embodiment, the report is communicated to the motion monitoring system (e.g., a user computing system or remote server) via a communication interface and/or a communications network. In another embodiment, the motion monitoring system may be included in a handheld tool and the reported motion log is accessed by the motion monitoring system to detect freezing events and make freezing predictions, as discussed herein. In embodiments, the reporting may be periodic, user initiated, initiated when a memory reaches a threshold capacity, initiated during charging, or otherwise initiated and transmitted to the motion monitoring system.

Figure 4:
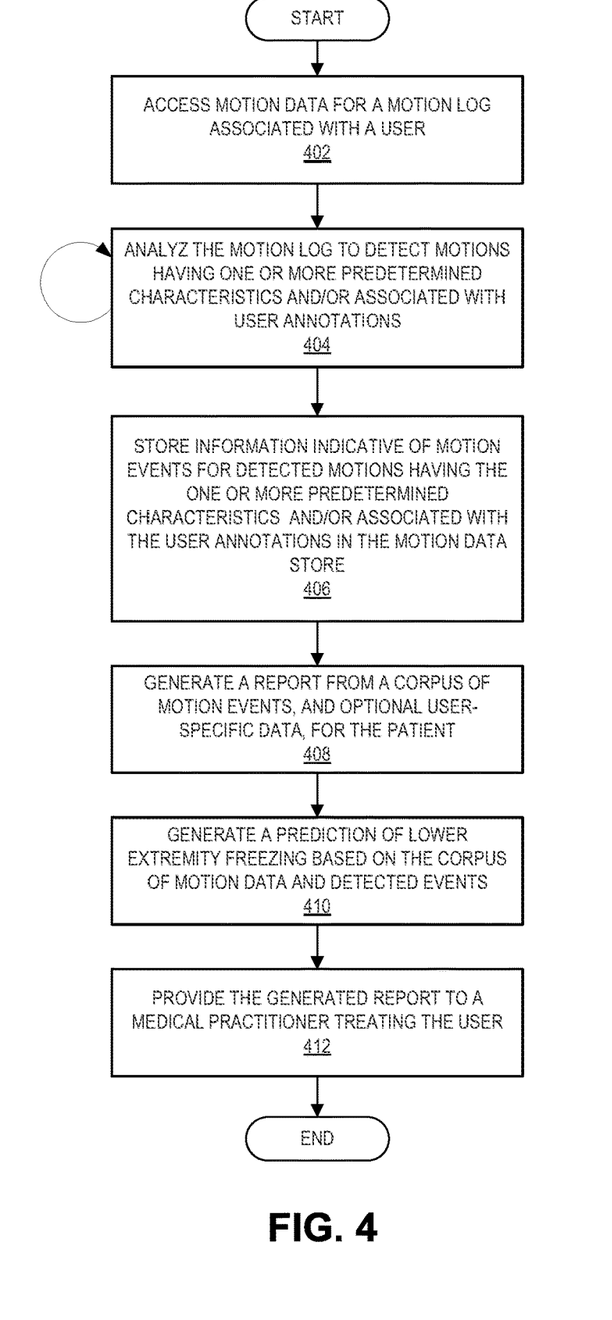
FIG. 4 is a flow chart illustrating a process for analyzing motion data to detect unintentional muscle movements, in accordance with an embodiment of the disclosure.

FIG. 4 is a flow chart illustrating a process for analyzing motion data to detect unintentional muscle movements, in accordance with an embodiment of the disclosure. The process is performed by processing logic that may comprise hardware (circuitry, dedicated logic, etc.), software (such as is run on a general purpose computer system or a dedicated machine), firmware, or a combination. In one embodiment, the process is performed by motion monitoring system (e.g., MMS 250 of FIG. 2) or a motion analysis subsystem of tremor tracking module (e.g., motion analysis subsystem 240 of FIG. 2).

The process begins ay accessing motion data for a motion log associated with a patient (processing block 402). As discussed herein, the motion data may be stored in motion logs maintained on a handheld tool, by a computer system that is periodically communicably coupled with a handheld tool, or in a data store maintained on a server computer system. Furthermore, the motion data can include monitored motions tracked over a period of time, including annotation associated with those motions. In one embodiment, the motion logs include tracking information of the user's motions over a period of time with sufficient information to enable processing logic to recreate or model the patient's motions.

Processing logic analyzes the motion log to detection motions having one or more predetermined characteristics and/or associated with user annotations (processing block 404). In one embodiment, the motions being detected are upper limb freezing events, where a patient's upper extremities involuntarily freeze for a period of time. Furthermore, information associated with the upper limb freezing, such as duration and severity are also extracted from the motion data. Such freezing events, and the characteristics associated with those events, can be detected by processing logic, for example, by analysis of the motion data to detect motions with certain frequency and/or amplitude user movements. As another example, processing logic may analyze the motion data to detect a first, precursor motion followed within a threshold period of time by a second, event motion (e.g., hastened movement with a strong amplitude breakdown followed within a predetermined period of time by small amplitude movements). In one embodiment, one or more motion signatures that model the characteristics of interest may be used by processing logic to match the user motions with the motion signatures in order to detect certain motion signature. Furthermore, user annotations may explicitly signal motion events, such as upper limb freezing events, and the motion data associated with those events.

Processing logic stores information indicative of the motion events for detected motions having the one or more predetermined characteristics and/or associated with the user annotations in the motion data store (processing block 406). Processing logic utilizes the stored information to generate a report from a corpus of motion event data, and optional user-specific data, for the patient (processing block 408). In one embodiment, processing logic utilizes the corpus of motion data and detected events to generate a detailed summary of the patient's freezing events, including one or more of a history of freezing events, a frequency of freezing events, a trend analysis of the patient's freezing events (e.g., increasing decreasing frequency, severity, length, etc.), a correlation to the history or trend analysis with patient medications, treatments, etc. (when available), as well as other information relevant to tracking user freezing events.

Processing logic further generates a prediction of lower extremity freezing based on the corpus of motion data and detected events (processing block 410). In one embodiment, processing logic utilizes the summarized freezing event data to predict lower extremity freezing utilizing one or more of duration, frequency, and/or severity of upper extremity freezing events. Additional information, such as trend analysis, history analysis, data associated with individual freezing events (e.g., events meeting specific threshold levels of duration and/or severity), etc. can be used to predict lower extremity freezing from detected upper extremity freezing events.

Processing logic then provides the report, with the prediction of the lower extremity freezing, to a medical practitioner treating the user (processing block 412). In one embodiment, this report is communicated electronically over a communications network, such as the Internet, in a secure manner to a health professional system accessible by the medical practitioner. The practitioner would therefore receive a dense assessment of upper extremity freezing and a prediction of lower extremity freezing. When correlated with medications, dosages, treatments, etc., with the reporting or by the practitioner, the practitioner is able to make a better plan for treatment, is able to more accurately diagnose a patient's conditions, and is able to monitor whether a current course of treatment and/or medication is effective in reducing upper and/or lower extremity freezing. The improvements in the diagnosis and treatment of the patient suffering from upper and/or lower extremity freezing has strong advantages for improving the quality of life and long-term care for the patient.

Figure 5:
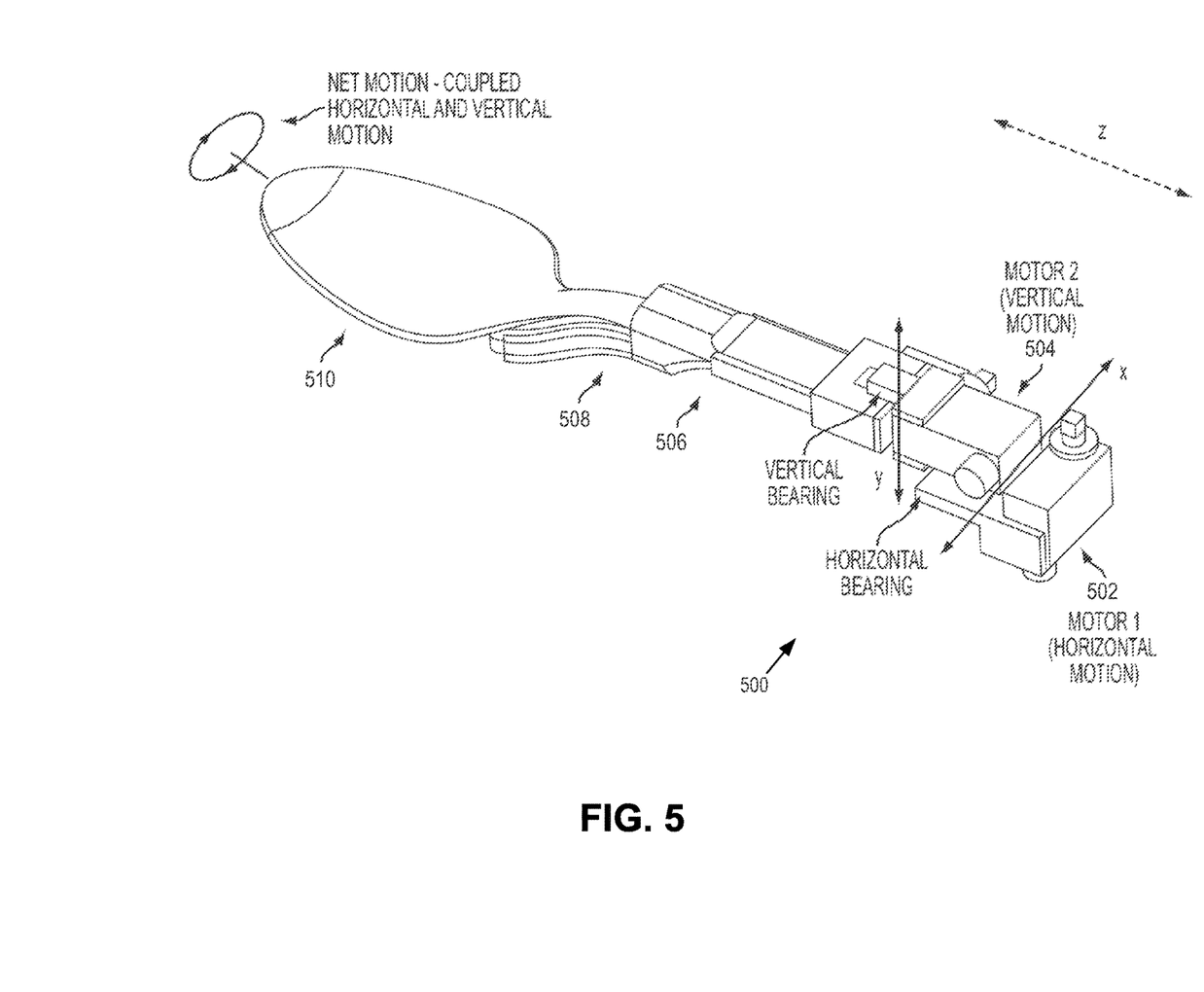
FIG. 5 is a perspective view illustration of a motion generating mechanism of a handheld tool that compensates for unintentional muscle movements, in accordance with an embodiment of the disclosure.

FIG. 5 is a perspective view illustration of a motion generating mechanism 500 of a handheld tool that compensates for unintentional muscle movements, in accordance with an embodiment of the disclosure. Motion generating mechanism 500 is one possible implementation of motion generating mechanism 114 illustrated in FIGS. 1A and 1B.

Motion-generating mechanism 500 includes a first miniature gear-reduction system coupled to a first coreless micro-motor 502 and a second miniature gear-reduction system coupled to a second coreless micro-motor 504. At least one inertial sensor 508 is placed along an attachment arm 506. The attachment arm 506 is configured to accept a user-assistive device 510 thereto.

The first coreless micro-motor is capable of producing rotary motion in the horizontal (x) direction. This rotary motion is imparted to the second coreless micro-motor through a rigid connection that is supported by a horizontal bearing. The second coreless micro-motor is capable of producing motion in the vertical (y) direction. This motion from the second coreless micro-motor is supported by a vertical bearing.

A coupling mechanism is used to combine the horizontal and vertical motions of the two separate coreless micro-motor/miniature gear-reduction systems 502 and 504. This combination results in a bi-directional circular motion of the user-assistive device 510 (in the illustrated embodiment, a spoon). One of ordinary skill in the art readily recognizes that a system and method in accordance with the present disclosure may utilize a variety of coupling mechanisms including but not limited to sliding bearing mechanisms, gimbal structures, or bellows structures and that would be within the spirit and scope of the present disclosure.

In the motion-generating mechanism 500, two degrees of freedom are generated from the two separate coreless micro-motor/miniature gear-reduction systems 502 and 504. Additional degrees of freedom (e.g., a third in the z-direction) can be added to the motion-generating mechanism 500 by adding motion to the output of the first coreless micro-motor or the output of the second coreless micro-motor.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method for measuring upper extremity freezing, the method comprising:
   sensing motions of a handheld tool with a motion sensor mounted in or on the handheld tool;
   receiving signals output from the motion sensor of the handheld tool, the signals indicating the motions of the handheld tool when used by a user during a period of activity;
   analyzing, by a processor, the motions of the handheld tool;
   detecting, by the processor, motions of the handheld tool having one or more predetermined characteristics; and
   determining, by the processor, that the user experienced the upper extremity freezing while using the handheld tool during the period of activity based on the detected one or more predetermined characteristics.

2. The method of claim 1, further comprising:
   determining one or more of a duration and a severity of the upper extremity freezing from the analysis of the motions having the one or more predetermined characteristics; and
   storing a record of the upper extremity freezing, wherein the record is associated with the user and comprises data indicative of one or more of the duration and the severity of the upper extremity freezing.

3. The method of claim 2, further comprising:
   analyzing severity and duration of upper extremity freezing experienced by the user from one or more records of upper extremity freezing associated with the user;
   determining a frequency of upper extremity freezing experienced by the user from the one or more records; and
   generating a prediction that the user has experienced lower extremity freezing based, at least in part, on one or more of the severity, duration, and frequency of upper extremity freezing experienced by the user.

4. The method of claim 3, further comprising:
   generating a report that summarizes the upper extremity freezing and includes the prediction that the user has experienced lower extremity freezing; and
   providing the report to a health professional system via a communications network.

5. The method of claim 4, wherein the generated report comprises one or more of (i) a first trend analysis of one or more of the frequency, severity, and duration of upper extremity freezing experienced by the user, (ii) a second trend analysis of a likelihood that the user has experienced lower extremity freezing based on severity, frequency, and duration associated with one or more predictions of upper extremity freezing, (iii) a correlation between the one or more of the first trend analysis and the second trend analysis, and (iv) a correlation between one or more of the first trend analysis and the second trend analysis with one or more of a medication associated with the user, a treatment of the user, and a diagnosis of the user.

6. The method of claim 1, wherein detecting motions comprises matching motions of the handheld tool against one or more motion signatures, wherein the motions signatures model motions having one or more predetermined characteristics of interest for detecting upper extremity freezing.

7. The method of claim 1, wherein detecting motions of the handheld tool having one or more predetermined characteristics further comprises:
   detecting an annotation associated with one or more motions of the user, wherein the annotation is user inputted data into the handheld tool that indicates that the one or more motions associated with the annotation correspond to a user condition comprising one or more of upper extremity freezing, lower extremity freezing, gait disorder, or imbalance experienced by the user during the period of activity; and
   storing a record that associates the user condition in the detected annotation with the one or more motions of the user associated with the detected annotation.

8. The method of claim 1, wherein the determining includes determining that the user has experienced upper extremity freezing when the one or more predetermined characteristics of the detected motions comprise a first motion having a first predetermined characteristic and by a second motion having a second, different predetermined characteristic, wherein the second motions occurs within a threshold period of time after the end of the first motion.

9. The method of claim 8, wherein the predetermined characteristic associated with the first motion comprises hastened motions having strong amplitude movements, and the predetermined characteristic associated with the second motion comprises small amplitude movements.

10. The method of claim 1, wherein the determining includes determining that the user has experienced upper extremity freezing when the one or more predetermined characteristics of the detected motions comprise an increased energy of the movements having a frequency between 3 Hz to 8 Hz.

11. A non-transitory machine readable storage medium having instructions stored thereon, which when executed by a processing system, cause the processing system to perform a method for measuring upper extremity freezing comprising:
   sensing motions of a handheld tool with a motion sensor mounted in or on the handheld tool;
   receiving signals output from the motion sensor of the handheld tool, the signals indicating motions of the handheld tool when used by a user during a period of activity;
   analyzing, by the processing system, the motions of the handheld tool;
   detecting, by the processing system, motions of the handheld tool having one or more predetermined characteristics; and
   determining, by the processing system, that the user experienced the upper extremity freezing while using the handheld tool during the period of activity based on the detected one or more predetermined characteristics.

12. The non-transitory machine readable storage medium of claim 11, further comprising:
   determining one or more of a duration and a severity of the upper extremity freezing from the analysis of the motions having the one or more predetermined characteristics; and
   storing a record of the upper extremity freezing, wherein the record is associated with the user and comprises data indicative of one or more of the duration and the severity of the upper extremity freezing.

13. The non-transitory machine readable storage medium of claim 12, further comprising:
analyzing severity and duration of upper extremity freezing experienced by the user from one or more records of upper extremity freezing associated with the user;
determining a frequency of upper extremity freezing experienced by the user from the one or more records; and
generating a prediction that the user has experienced lower extremity freezing based, at least in part, on one or more of the severity, duration, and frequency of upper extremity freezing experienced by the user.

14. The non-transitory machine readable storage medium of claim 13, further comprising:
generating a report that summarizes the upper extremity freezing and includes the prediction that the user has experienced lower extremity freezing; and
providing the report to a health professional system via a communications network.

15. The non-transitory machine readable storage medium of claim 14, wherein the generated report comprises one or more of (i) a first trend analysis of one or more of the frequency, severity, and duration of upper extremity freezing experienced by the user, (ii) a second trend analysis of a likelihood that the user has experienced lower extremity freezing based on severity, frequency, and duration associated with one or more predictions of upper extremity freezing, (iii) a correlation between the one or more of the first trend analysis and the second trend analysis, and (iv) a correlation between one or more of the first trend analysis and the second trend analysis with one or more of a medication associated with the user, a treatment of the user, and a diagnosis of the user.

16. The non-transitory machine readable storage medium of claim 11, wherein detecting motions comprises matching motions of the handheld tool against one or more motion signatures, wherein the motions signatures model motions having one or more predetermined characteristics of interest for detecting upper extremity freezing.

17. The non-transitory machine readable storage medium of claim 11, wherein detecting motions of the handheld tool having one or more predetermined characteristics further comprises:
detecting an annotation associated with one or more motions of the user, wherein the annotation is user inputted data into the handheld tool that indicates that the one or more motions associated with the annotation correspond to a user condition comprising one or more of upper extremity freezing, lower extremity freezing, gait disorder, or imbalance experienced by the user during the period of activity; and
storing a record that associates the user condition in the detected annotation with the one or more motions of the user associated with the detected annotation.

18. The non-transitory machine readable storage medium of claim 11, wherein the determining includes determining that the user has experienced upper extremity freezing when the one or more predetermined characteristics of the detected motions comprise a first motion having a first predetermined characteristic and by a second motion having a second, different predetermined characteristic, wherein the second motions occurs within a threshold period of time after the end of the first motion.

19. A system for measuring upper extremity freezing, comprising:
a memory to store motions of a handheld tool, the motions received from a motion sensor mounted in or on the handheld tool and indicating motions of the handheld tool when used by a user during a period of activity;
a processor coupled with the memory, the processor configured to:
analyze the motions to detect motions of the handheld tool having one or more predetermined characteristics, wherein the one or more predetermined characteristics include a first motion characteristic followed within a threshold period of time by a second motion characteristic, and
determine that the user experienced the upper extremity freezing while using the handheld tool during the period of activity based on the detected one or more predetermined characteristics.

20. The system of claim 19, further comprising the processor configured to:
determine one or more of a duration and a severity of the upper extremity freezing from the analysis of the motions having the one or more predetermined characteristics; and
store a record of the upper extremity freezing in the memory, wherein the record is associated with the user and comprises data indicative of one or more of the duration and the severity of the upper extremity freezing.

21. The system of claim 20, further comprising the processor configured to:
analyze severity and duration of upper extremity freezing experienced by the user from one or more records of upper extremity freezing associated with the user;
determine a frequency of upper extremity freezing experienced by the user from the one or more records; and
generate a prediction that the user has experienced lower extremity freezing based, at least in part, on one or more of the severity, duration, and frequency of upper extremity freezing experienced by the user.

22. The system of claim 21, further comprising the processor configured to:
generate a report that summarizes the upper extremity freezing and includes the prediction that the user has experienced lower extremity freezing; and
provide the report to a health professional system via a communications network.

23. The system of claim 19, further comprising the handheld tool, and wherein the handheld tool comprises:
a handle;
an attachment arm extending from the handle;
a user-assistive device attached to a distal end of the attachment arm;
an inertial measurement unit ("IMU") rigidly attached to the handle to measure motions of the handle, generate motion data indicative of the motions of the handle, and store the motion data in the memory;
a motion analysis subsystem to analyze the motion data and determine when the user has experienced upper extremity freezing; and
a communication interface to output a report based on the motion data to a health professional system via a communications network.

24. The system of claim 19, further comprising:
a motion monitoring system to analyze the motion data and determine when the user has experienced upper extremity freezing;

a communications interface to communicably couple the motion monitoring system with the handheld tool via a communications network; and
a practitioner interface to output a report based on the motion data to a health professional system via the communications network.

* * * * *